United States Patent [19]

Pugh

[11] Patent Number: 4,631,676
[45] Date of Patent: Dec. 23, 1986

[54] COMPUTERIZED VIDEO GAIT AND MOTION ANALYSIS SYSTEM AND METHOD

[76] Inventor: James W. Pugh, 115 E. 9th St., New York, N.Y. 10003

[21] Appl. No.: 497,823

[22] Filed: May 25, 1983

[51] Int. Cl.$^4$ ................................................ A61B 5/10
[52] U.S. Cl. .................................... 364/413; 128/782; 364/415
[58] Field of Search ........................ 364/413, 415, 559; 128/782, 774, 779

[56] References Cited

U.S. PATENT DOCUMENTS 4,267,728  5/1981  Manley et al. ........................ 128/779
4,375,674  3/1983  Thornton ........................... 128/782 X
4,416,293  11/1983  Anderson et al. .................... 128/782

OTHER PUBLICATIONS

*Computers and the Kinesiology of Gait;* T. Kasvand et al., Comput. Biol Med, vol. 6, pp. 111–120, 1976.
*Computer-aided Tracking of Body Motions Using a CCD-Image Sensor;* Brugger et al., Med & Bio Eng, 3/1978.

*Primary Examiner*—Jerry Smith
*Assistant Examiner*—Charles B. Meyer
*Attorney, Agent, or Firm*—Stephen E. Feldman

[57] ABSTRACT

A reflective marker is attached to the front and side of each joint of a subject whose motion or gait is to be analyzed. Each marker is formed of reflective tape and is relatively small and weightless and will not hinder or affect the subject's movements. A pair of Sony Video Motion Analyzers operating at sixty frames per second are positioned to the front and side of a walkpath having a marked centerline along which the subject walks; and coact with video cassette tape recorders to record the subject's movements along the runway. Monitors, provided for playback of the recorded video tape, are each provided with a built-in magnetic disk allowing ten seconds of high-speed motion to be recorded and displayed. A CAT-100 video analysis board, retrofitted into a Z 80 64K TE1 minicomputer, digitizes each recorded video frame to locate by x, y, (or z) coordinates the centroid of each marker and feeds the data into a PDP 11/70 computer which operates on the data to provide line and stick figure outputs of the data and which depict the motions under study; cyclograms of hip angle-knee angle relationships for a cycle of movement of the subject are also provided.

18 Claims, 11 Drawing Figures

COMPUTERIZED VIDEO GAIT AND MOTION ANALYSIS SYSTEM AND METHOD

BACKGROUND OF THE INVENTION

1. Field of Application

This invention relates to systems and methods for analyzing motion; and more particularly to a system and method for analyzing the movement of a portion or portions of a body.

2. Description of the Prior Art

Motion analysis, and more particularly analysis of the movement of specific parts of the human body such as arms or legs, is finding increased use and application in athletics and medically related fields. By analyzing the movement of a baseball player's arm it may be possible to suggest improvements in their swing and hopefully their batting average. More importantly, by analyzing the movement of a person's arm, hip, knee, foot, or other body part, it may be possible to suggest therapy or corrective surgery that will permit easier or less painful use of the body part, or prevent joint or bone deterioration or disorders.

However, observation of such motion by using only the human eye and on-the-spot mental analysis, has not proved definite and accurate enough to be effective. The motions are too quick in time and too lost in space to be accurately remembered or recorded. Additionally, it may be quite painful to the subject to keep repeating the motion so that the observer can perceive an accurate mental picture of the motion and make an on-the-spot analysis.

Various methods and systems have been created which utilize equipment to provide a sensible output related to the motion to be analyzed, and a record of the output so provided for use in analyzing the motion. Some of these systems make the record by use of motion photography and thus must wait the developing of the film to even determine if the desired motions were properly recorded for analysis purposes. Other systems require complex computer hardware and software packages and trained technicians thus greatly adding to the cost of the equipment itself and the acquisition and analysis of the data.

Quite often the motion analysis system requires the attachment of the subject by cables to remote sensors such as shown in an article by Strelow et al entitled "Apparatus For Measuring And Recording Path Velocity And Direction Characteristics of Human Locomotion" that appeared in *Behavior Research Methods and Instrumentation*, Vol. 8, No. 5, pp. 442–446, October 1976; or the placing on the subject of sensing devices that are in turn attached by electric cables to remote recording devices such as described in an article by Smidt et al, entitled "An Automated Accelerometry System For Gait Analysis" that appeared in *J. Biomechanics*, Vol. 10, No. 5–6, 1977 pp. 367–375, or as shown in U.S. Pat. No. 3,699,856 granted on Oct. 24, 1972 to R. W. Chiabot et al for Movement Monitoring Apparatus. The attachment to the subject of equipment or devices having any weight factor will most probably modify the body motion to be analyzed and add a variable to the analysis and calculations that may be difficult, if not impossible, to factor out. Furthermore the attaching to the subject of cables, electric or otherwise, not only adds an additional weight factor but may also impede and possibly modify the motion under study.

The subject under study may be somewhat less restricted in their movement by devices such as those shown in U.S. Pat. No. 3,717,857 granted to J. W. Evans on Feb. 20, 1973 for Athletic Swing Measurement Systems which utilize a radio transmitter to send the sensed signal to a remote receiver. But they must still carry a motion sensing device and radio transmitting apparatus. The weight and location of such devices may still affect the motion being sensed and add to the analysis variables which cannot be factored out.

The subject can be freed of attached devices and cables by providing a surface and sensors responsive to the subjects motions upon the surface such as the force plate/piezoelectric sensor combination shown in U.S. Pat. No. 3,894,437 granted to J. L. Hogy on July 15, 1975 or Method And Means For Dynamic Gait Analysis, or the mattress and capacitive motion sensor combination shown in U.S. Pat. No. 4,320,766 granted to J. Alihanka, et al on Mar. 23, 1982 for Apparatus in Medicine For The Monitoring And Or Recording of The Body Movements Of a Person On A Bed, For Instance Of A Patient. However, the equipment and method of the later patent is of little utility if the body motion to be monitored requires walking or similar body movement; while force plates are usually of limited size and may not be suitable if the problem under study becomes more pronounced with continued body motion over a period of time.

SUMMARY OF THE INVENTION

It is therefore an object of this invention to provide a new and improved system for motion analysis.

It is another object of this invention to provide a new and improved method for motion analysis.

It is yet another object of this invention to provide a new and improved system for gait analysis.

It is still another object of this invention to provide a new and improved method for gait analysis.

It is yet another object of this invention to provide a system and method for observing and recording the gait of a human being and for analysis of said gait.

It is yet still another object of this invention to provide a new and improved system and method for observing and recording the characteristics of the gait of a person whose gait may be other than normal and for analyzing said gait characteristics and comparing same against the gait of a person considered to have normal gait characteristics.

It is yet still a further object of this invention to provide a new and improved system and method for observing and recording the motion characteristics of a portion of the body of a person and for analyzing such characteristics; which system and method does not require the continued presence of the subject under study while the characteristics so studied are being analyzed.

This invention involves a system and method for observing and recording the characteristics of a segment of the body while in motion, such as gait; and the subsequent analysis of such characteristics for purposes such as modification, correction, improvement, or any desired purpose. The invention contemplates: the placement upon the test subject of one or more sensible markers of insignificant weight and which will neither modify nor restrict the body motion under study; the video recording of the motion of the marked body segment under study over a selected period of time so that there can be immediate observation of the characteristics so recorded as well as a reusable hard copy thereof; the computerized analysis of the characteristics so recorded; and the provision of hard copy, angle diagrams, line and/or stick figure outputs of the computerized analysis.

Other objects, features, and advantages of the invention in its details of construction and arrangement of parts will be seen from the above, from the following description of the preferred embodiment when considered with the drawing and from the appended claims.

BRIEF DESCRIPTION OF THE PREFERRED EMBODIMENT

For convenience, the invention will be described as applied to a motion analysis system and method wherein the test subject is an adult male dressed in a skin tight garment such as a leotard and having markers in the form of relatively small pieces of reflective adhesive tape disposed on the side and front of his hip, knee, and ankle joints respectively. The test subject walks for a fifteen minute period along a walkway having its centerline marked and before a pair of Sony Motion Analyzer Video Cameras specially equipped with a rotating shutter to film at sixty frames per second. The camera output is recorded on three-fourth inch video tape on a Sony Umatic Video casette recorder and is viewable on monitors having ten seconds of high speed motion to be recorded and displayed. The TV images are analyzed by a Z-80 64K TE1 Incorporated microcomputer retrofitted with a CAT-100 video board and which serves as the input to a Digital Equipment Corp. PDP 11/70 computer interfaced with a Tektronik 4012 graphics terminal, a Tektronick 4662 plotter, and a Tektronik 4631 hard copy unit. It should be understood, nevertheless, that without departing from the scope of this invention: that the test subject can be adult or child, male or female; that the markers can be of any suitable reflective substance which neither adds weight to nor hinders the motion of the test subject; that the joint motion to be analyzed can be that of any combination of joints; that the testing time period can be any suitable and appropriate time interval; and that the cameras, video recorders, microcomputer, computer, terminals, plotter and hard copy unit can be of any suitable and appropriate manufacture.

Figure 1:
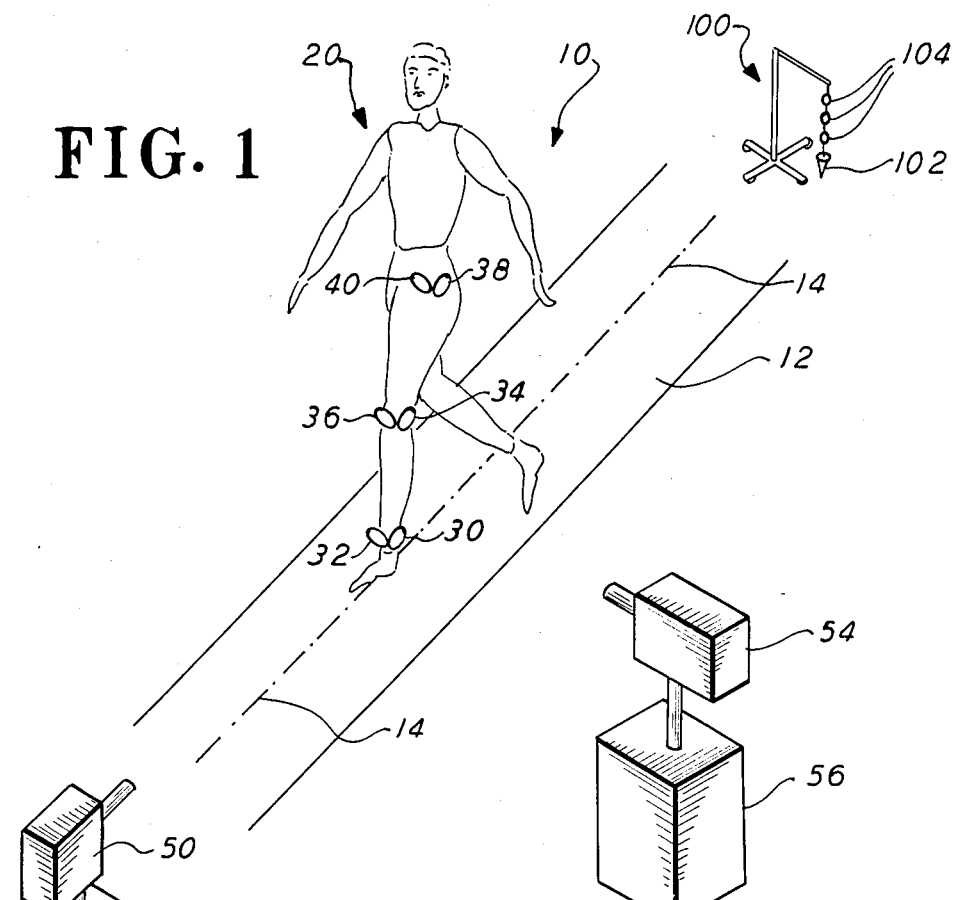
FIG. 1 is a schematic isometric showing of a test subject in motion before the recording apparatus of the system and method incorporating the instant invention.

With reference to FIG. 1 there is generally shown at 10 an adult male test subject walking along a walkway 12 having its centerline 14 marked as by paint, tape or other suitable substance. Test subject 10 is wearing a leotard type garment 20 which provides suitable cover while permitting their movements to be unhindered and observable.

Pieces of reflective marking tape are applied to the test subjects joints at the side 30 and front 32 of their ankle, at the side 34 and front 36 of their knee, and at the side 38 and front 40 of their hip. Markers 30-40 are approximately one inch squares of tape with a suitable and conventionally available reflective coating applied to their surfaces. Markers 30-40 are located as close to the center of their respective joints as possible. Other suitable substances and sizes may be used.

Figure 2:
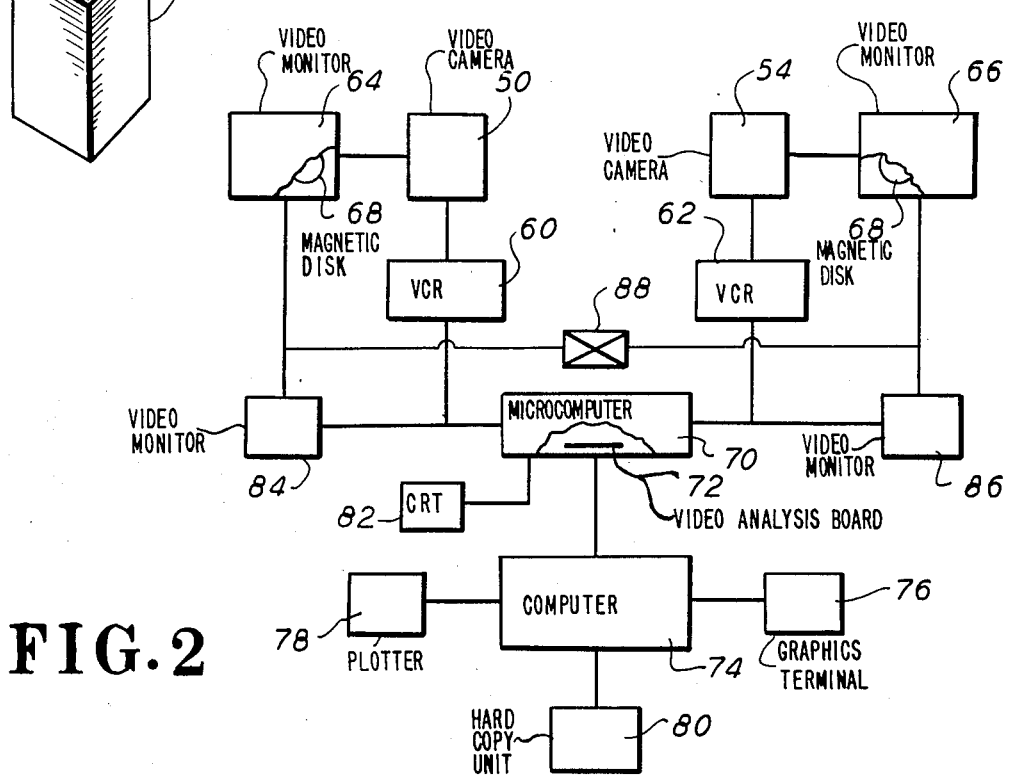
FIG. 2 is a schematic block diagram of the apparatus for the system and method of the instant invention.

A first video camera 50 is disposed on a suitable platform or stand 52 to record the movement of test subject 10 from the front; while a second video camera 54, disposed on a suitable platform or stand 56, is positioned to record the movement of test subject 10 from the side. Video cameras 50, 54 (FIGS. 1 and 2) are conventionally available Sony Motion Analyzers rendered specially sensitive to reflective markers 30-40; and which are specially equipped with rotary shutters 58 to provide for filming at sixty frames per second.

The filming by cameras 50, 54 continues for the selected time period while test subject 10 performs their particular motion. In this particular example test subject 10 is walking because their gait is being studied and analyzed. The time period selected is fifteen minutes, however, more or less time may be utilized depending upon the desires of the party conducting the test.

Video recorders 60, 62 are suitably connected to video cameras, 50, 52 respectively to provide a record of the movements of test subject 10 for later analysis. Recorders 60, 62 are Sony Umatic Video cassette recorders which record upon standard three-quarter inch video tape. Other suitable recorders and tape size may, however, be used. During recording, the movements of test subject 10 may also be viewed on TV monitors 64, 66 of conventional construction and suitably connected to cameras 50, 52 and recorders 60, 62 respectively. Monitors 64, 66 are specially equipped with a built-in magnetic disc 68 sized, selected and suitably connected to provide ten seconds of high-speed motion to be recorded and displayed in either reel-time or stop-frame.

A Z-80 64K microcomputer 70 is suitably connected into the system to receive the images recorded on discs 68 of monitors 64, 66. Microcomputer 70 is a hybrid from TE1 Incorporated and is retrofitted with a CAT-100 video analysis board 72 of conventional construction. Connected to microcomputer 70, by conventional wiring and controls is a Digital Equipment Corporation PDP 11/70 Computer 74. The interfacing of microcomputer 70 with computer 74 allows much more efficient use of microcomputer 70 while increasing the number-crunching capacity through computer 74. Microcomputer 70 and computer 74 are equipped with suitable firmware and software and are otherwise user friendly and programmable to carry out the motion analysis as will be hereinafter described. A Tektronik 4012 graphics terminal 76, a Tektronik 4662 plotter 78, and a Tektronik 4531 hard copy unit 80 are all suitably connected and interfaced with computer 70. A Hazeltime Cathode ray terminal 82 and standard TV video monitors 84, 86 are suitably connected to microcomputer 70; while a custom switching box 88 is suitably and conventionally connected to video monitors 64, 66, 84, and 86 and is provided with controls to allow efficient conversion between display, acquisition, and analysis modes for monitors 64, 66, 84 and 86.

A calibration test stand 100 (FIG. 1), provided with a plumb bob 102 and reflective test markers 104, when appropriately positioned with respect to video cameras 50, 54 allows for exact assessment of true vertical. The spacing of test markers 104 allows calibration of scaling factors.

At the start of each days motion testing test stand 100 is positioned with respect to video cameras 50, 54 to ensure that cameras 50, 54 are perpendicular to each other. A special calibration program is then run and the magnification factors, perpendicular alignment, linearity, and parallax factors are calculated for each camera 50, 54 and stored in computer 74. These factors, due to changing set-ups of cameras 50, 54 are unique for a particular set of tapes and are applied only to those tapes to ensure data integrity.

Test subject 10 has markers 30, 32, 34, 36, 38 and 40 applied as hereinbefore explained. Markers 30–40 are applied to the joints of the hip, knee and foot because the gait of test subject 10 is to be analyzed. Markers 3040 are of negligible weight and will not in any way affect or modify the gait of test subject 10. Test subject 10 thereafter walks along runway 12 along centerline 14 thereof and in view of video cameras 50, 54 for a selected period of time sufficient to gather an appropriate data sample. While walking test subject 10 can be viewed on monitors 64, 66 and initial impressions can be obtained by the test supervisor.

Recorders 60, 62 record the movements of test subject 10 on the video casettes throughout the entire test. Since the movements of test subject 10 are thus recorded the analysis phase of the test can take place from the recorded data and without test subject 10. However, if a particular motion of developmental interest is observed during the test an analysis thereof can be performed on-line and while test subject 10 is marked.

Figure 3:
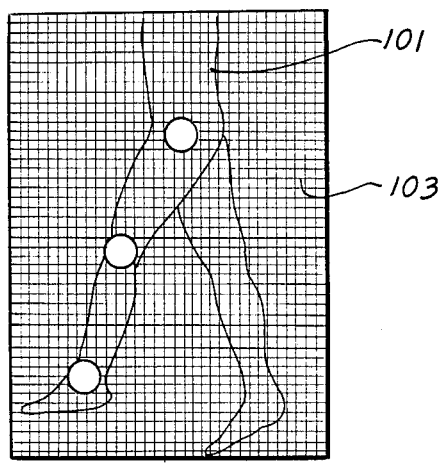
FIG. 3 is a schematic showing of a digitized image of the side view of the test subject of FIG. 1.
Figure 4:
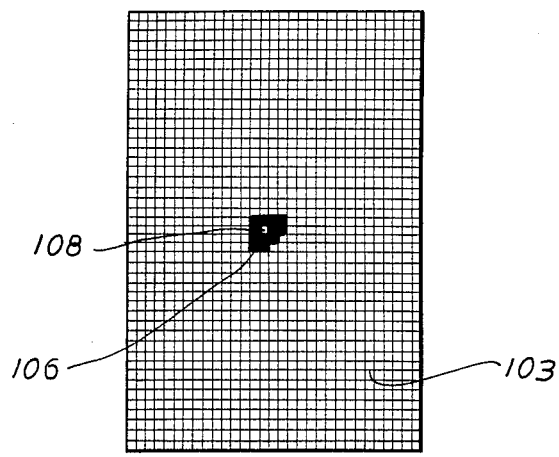
FIG. 4 is a schematic showing of computer blacked-in pixels, associated with the hip joint marker of the test subject of FIGS. 1 and 4, indicating the geometric centroid thereof.

Following data acquisition the video casettes are rewound and played back into magnetic discs 68. Each image 101 (FIG. 3) so recorded is sequentially digitized as shown in FIG. 3 by CAT-100 board 72 and displayed on monitors 84, 86. Image 100 consists of an array of pixels 103 of which there are 288 horizontally displayed and 228 vertically displayed. Each pixel 103 has a gray level from zero to 15. The location of each pixel 103 on TV monitors 84, 86 bears a determinable relationship to the position in three-dimensional space of the point that generated the particular pixel 103. By suitable programming CAT-100 board 72 scans video image 101 and stops at pixel 103 of brightness above a predetermined threshold. Computer 74 then determines the x, y, (or z) coordinates (on monitors 84, 86) of the position of the particular pixel 102 and thereby of marker (30–40) over a particular body site. When marker (30–40) has been so located the computer program will black-in the brightest pixels 103 as shown at 106 in FIG. 4 and will indicate the geometric centroid 108 of these brightest pixels 103.

The computer will thereafter search for the next marker (30–40).

The first four centroids 108 are indexed by hand, and subsequent frames, at 1/60-second intervals, are analyzed automatically through the programming provided. The only data needed and accordingly the only data taken from each frame are the x and y (or z) coordinates of markers (30–40) and the gray level of the spot. The memory of CAT-100 board 72 are cleared after each frame is so analyzed and the 288 by 228 array of pixels for the next frame is set up for analysis.

Some errors indetermination of the location of the position of markers (30–40) are introduced by changing gray level, due to slight rotation of a marker (30–40) out of the plane of the TV cameras, by fore-shortening of the marker by rotation; and by blockage of the marker by a swinging hand during walking. The software provided takes all of these into consideration. Several other techniques are available to locate markers (30–40). If the gray level changes during motion such that the reflectivity of the marker falls below the predetermined threshold, computer 74 automatically adjusts the threshold to a lower gray level enabling the marker to be found in subsequent frames. If the marker has been blocked by a swinging hand, the computer flags this and subsequently interpolates between identical points to find the missing point, and thus provides a complete set of data. The software also provides a cross-coupling feature that allows the data from front camera 50 to be corrected by data from side camera 54 and vica versa, to further eliminate magnification and parallax. The x, y and z coordinates for each point are available by print-out from computer 74 and hard copy unit 80.

The method and system provided results in a determination of the position of markers (30–40) to about plus or minus 0.3 cm, absolute accuracy and a reproducibility of greater than 99%. The results produce data of high enough integrity to be clinically useful.

Figure 5:
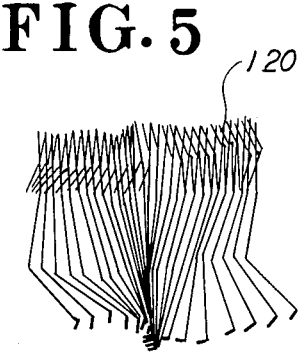
FIG. 5 is a showing of the multiple stick figure display of side view motion of the test subject of FIGS. 1, 3 and 4.
Figure 6:
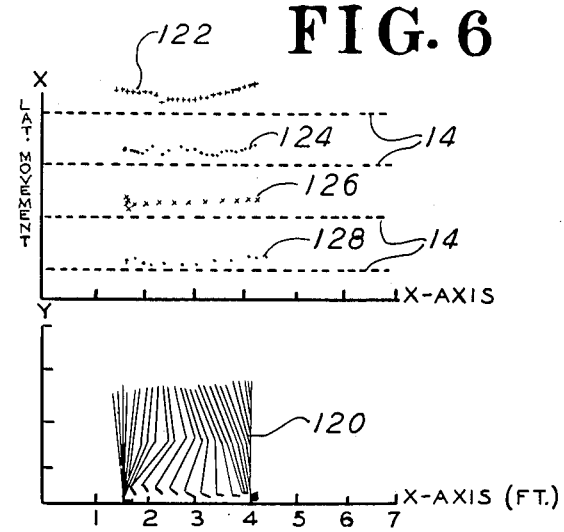
FIG. 6 is a hard copy line and multiple stick figure showing of the motion of the test subject of FIGS. 1, 3 and 4.

After all x, y, and z coordinates have been determined for each frame of the video record for the body segments and joints of interest the data so collected is dumped into microcomputer 70 for analysis, final calculations and data presentation. One program produces stick FIGS. 120 (FIGS. 5 and 6) of test subject 10 of any degree of complexity upon operator request. Since x, y, and z coordinates for each marker for each frame are stored in computer 74 an overhead view of the movement thereof is easily depicted in the form of deviation of the markers from centerline 14 of runway 12. This is shown in FIG. 6 with respect to display thereof of centerline 14 for hip marker spots 122, knee marker spots 124, ankle marker spots 126, and toe marker spots 128. This data and its display as shown in FIG. 6 are potentially useful in the determination of out-of-plane motions relevant to the assessment of orthopedic disorders.

Stick figures have value and the advantage of providing an analog display of data produced by computer 74 that bears a direct relationship to the actual motion of the patient. The usefullness of this data lies in its interpretability. Stick figures are especially of practical value when test subject motion is extremely abnormal.

Figure 8A:
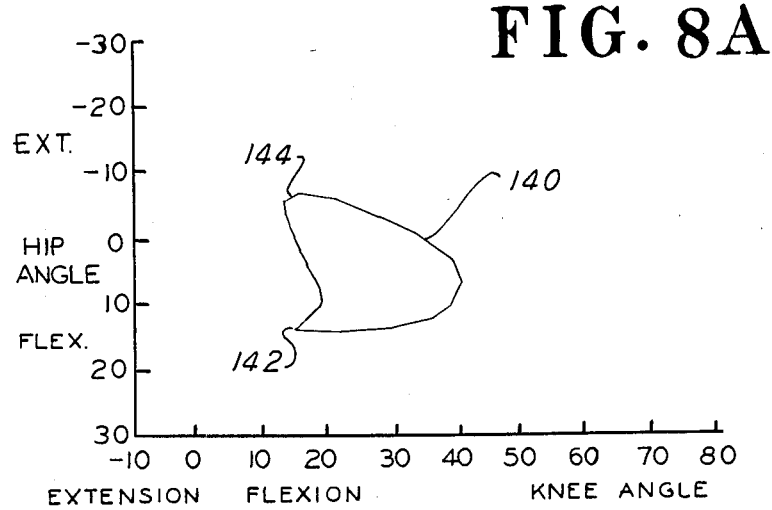
FIGS. 8a and 8b are hip angle-knee angle diagrams, similar to the one of FIG. 7, but before and following respectively a specified type of knee surgery.
Figure 8B:
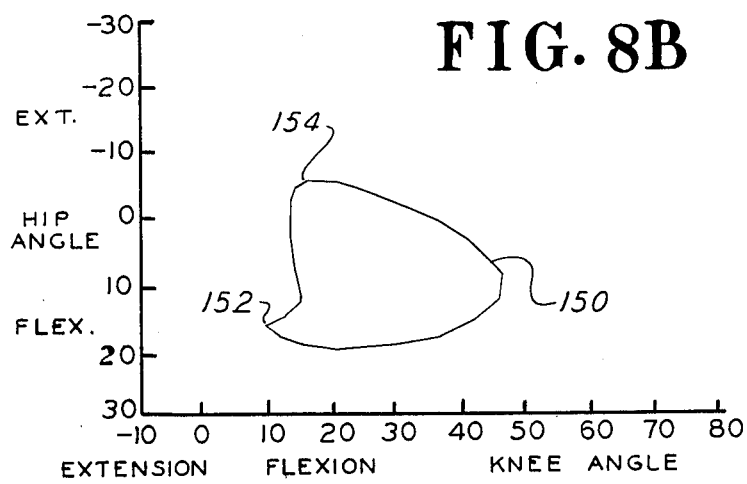
Figure 9A:
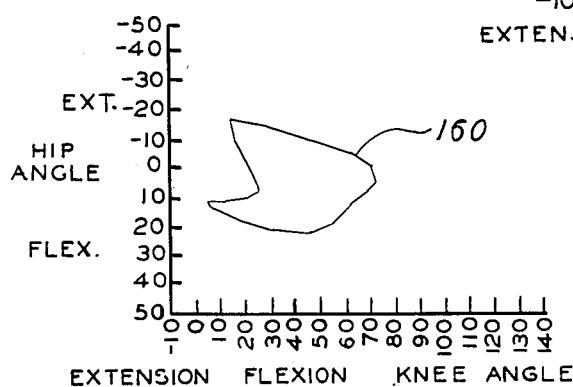
FIGS. 9a and 9b are hip angle-knee angle diagrams, similar to the one of FIG. 7, but for a normal runner wearing respectively a first and a second style or running shoes.
Figure 9B:
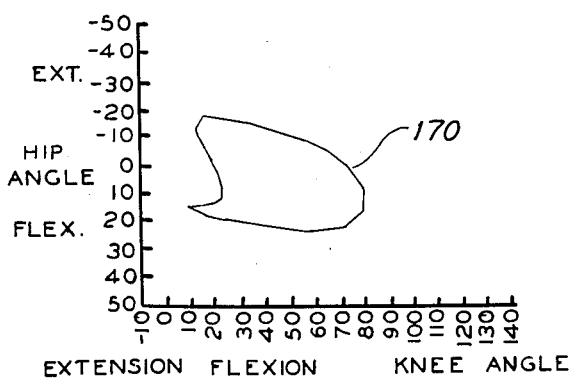

A subroutine is also provided for computer 74 to produce cyclograms, from the three dimensional data, such as those shown at 130 (FIG. 7), 140 (FIG. 8a), 150 (FIG. 8b), 160 (FIG. 9a), and 170 (FIG. 9b). Cyclograms 130, 140, 150, 160 and 170 depict the angular relationship of two joints during a cycle of motion. The degree of smoothness and openness of the cyclogram has been found to be a good indicator of the relative normalcy of the motion. Certain orthopedic conditions can be quantitated quite readily through such a depiction of the angle-plot, by comparison with similar data from a typical normal test subject.

Figure 7:
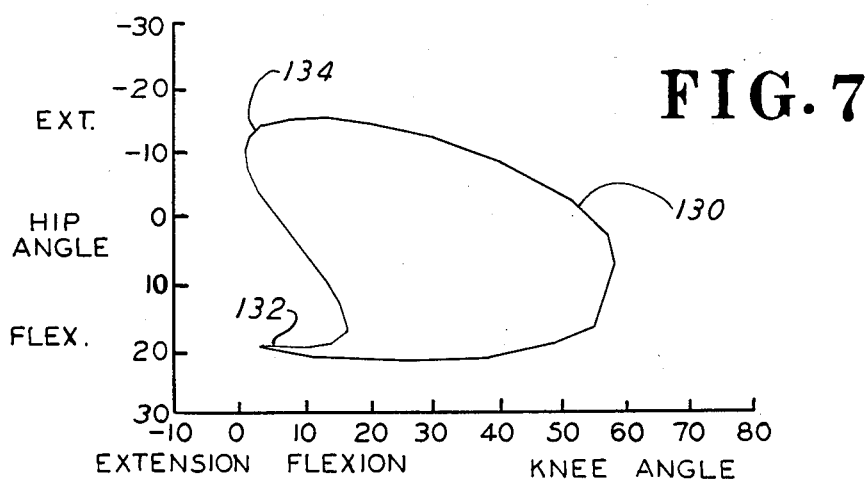
FIG. 7 is a hip angle-knee angle diagram for a normal test subject as generated by the system and method of the instant invention.

For example, FIG. 7 shows a hip angle (vertical coordinate) knee angle (horizontal coordinate) cyclogram 130 for a normal test subject. The heel-strike 132, and toe-off 134 positions are shown. The progression is clockwise with the bulk of the curve from toe-off position 134 to heel-strike position 132 representing the swing phase of walking. FIG. 8a on the other hand, shows a cyclogram 140 for a rheumatoid arthritic prior to right knee synovectomy. Heel-strike position 142 and toe-off position 144 are shown. The difference between cyclogram 140 and cyclogram 130 are obvious and the difference between the relative degrees of openness depicts a kinematic compromise. FIG. 8b shows cyclogram 150 for the same subject as that of cyclogram 140 but five weeks following corrective surgery. Cyclogram 150 approaches the normal openness of that of cyclogram 130 and indicates significantly improved kinematics for this subject.

Running gait differs from walking gait in that it has a float phase, in which the subject is competely off the ground for a fraction of the motion cycle. Cyclograms 160 (FIG. 9a) and 170 (FIG. 9b) shown hip-angle/knee-angle relationships for a runner wearing two different styles of running shoes. Cyclogram 160 shows irregularities in the motion while cyclogram 170 depicts a change towards normal.

Angular and linear accelerations are readily generated by simple differentiation of the three dimensional positional data. Coupling these data with information about the mass characteristics of the body segments analyzed allows determination of the forces necessary to produce the observed motions. Thus, an application of kinetic considerations to the kinematic data results in information on muscle forces that generated the observed accelerations. Once the muscle forces are known, a simple algorithm generates the joint forces throughout a cycle of motion.

The data, stick figures, and cyclograms generated by the described system and method provides orthopedic surgeons and neurologists interested in gait with a new tool useful in both diagnosis and treatment. It permits gait to be broken down into its varying parts and permits better identification and evaluation of abnormalities and of the results of the corrective procedures taken with respect thereto.

From the above description, it will thus be seen that there has been provided a new and improved system and method of video motion and gait analysis; which motion analysis system and method does not use attachments which impair, obstruct or modify the motion to be studied, utilizes user-friendly equipment, and minimizes human error in the acquisition and analysis of the data.

It is understood that although I have shown the preferred formed of my invention that various modifications may be made in the details thereof without departing from the spirit as comprehended by the following claims.

I claim:

1. A motion analysis system for analyzing the movements of a portion of the body of a subject as it moves along a predetermined path; comprising:

(a) marking means of relatively small size and weight in comparison to the size and weight of the subject and being attachable to the subject so as not to modify or hinder the movement of the subject;
    (b) video recording means for viewing and making a video record of the movements of the subject over a predetermined period of time, and at a recording rate of sixty frames per second, said video recording means being formed to be particularly sensative to said marking means;
    (c) minicomputer means connected to said video recording means and coacting therewith for receiving frame by frame views of the movements of the subject and more particularly the images of said marking means as viewed by said video recording means;
    (d) said minicomputer means including video analysis means for receiving and for sequentially digitizing, into a predetermined array of pixels, each of said views of said movement of said subject and said marker as viewed by said video recording means;
    (e) each said pixel having predetermined horizontal and vertical coordinates with respect to horizontal and vertical reference lines and having a gray level corresponding to the brightness of that part of the image represented by said pixel and particularly the brightness of the image of said marking means as viewed by said video recording means;
    (f) first program means coacting with said minicomputer to effect scanning of each said pixel array and for setting a first threshold of gray level above which said minicomputer will respond and provide a predetermined indication thereof, and for changing said first threshold to a second threshold of gray level when said minicomputer fails to respond to a pixel of at least said first threshold of gray level in a frame at the approximate horizontal and vertical coordinates of a pixel previously responded to by said minicomputer in the previous last scanned frame;
    (g) said first program means coacting with said minicomputer to locate, by x and y type data coordinates, each of said pixels responded to by said minicomputer for each frame so viewed and to record same, and to thereafter automatically and similarly locate each of said pixels having at least the gray level established by said first program for such pixel for all of said frames so viewed and to record same;
    (h) computer means coacting with said minicomputer means for receiving said pixel data coordinates and for combining same into a predetermined data display;
    (i) and data output means coacting with said computer means for providing a visual depiction of said predetermined data display.

2. The motion analysis system of claim 1, wherein said marking means includes a plurality of markers each of which has a reflective surface which, when said markers are attached to the subject, are disposed for viewing by said video recording means;

3. The motion analysis system of claim 2, wherein each said marker is adhesively attached to the subject at a joint of the subject.

4. The motion analysis system of claim 1, wherein said video recording means includes video camera means and video casette tape recording means.

5. The motion analysis system of claim 4, wherein said video recording means includes video monitor means having magnetic disc means constructed to record and display a predetermined time interval of motion in either reel-time or stop-motion.

6. The motion analysis system of claim 5, wherein said predetermined time interval is ten seconds.

7. The motion analysis system of claim 6, wherein:
   (a) said video camera means includes at least two video cameras and said video casette tape recording means, includes at least two video casette tape recorders each disposed and connected for coaction with one of said video cameras;
   (b) a first one of said video cameras being disposed at a first predetermined angle with respect to said predetermined path, and a second one of said video cameras being disposed at a second predetermined angle with respect to said predetermined path;
   (c) said marking means including a plurality of markers at least one of which is attached to the subject to be viewed by said first camera as the subject moves along said predetermined path, and at least another of said markers is attached to the subject to be viewed by said second camera as the subject moves along said predetermined path;

8. The motion analysis system of claim 7, wherein said first predetermined angle is such as to view the subject from their side and said second predetermined angle is such as to view the subject from its front, said markers being appropriately attached.

9. The motion analysis system of claim 8, wherein said first predetermined angle is disposed at ninety degrees with respect to said second predetermined angle.

10. The motion analysis system of claim 9, wherein there are a plurality of markers attached to the subject there being a pair of said markers for each joint to be analyzed, one of said markers of each of said pairs attached to the subject to be viewed from the front and the other of said markers of each of said pairs attached to the subject to be viewed from the side.

11. The motion analysis system of claim 9, wherein said computer means includes other program means to gather and combine data gathered from predetermined pixels in each pixel array from markers attached to the front and side of the subject.

12. The motion analysis system of claim 1, wherein said data output means provides a stick figure depiction of the motion of the subject.

13. The motion analysis system of claim 1, wherein said data output means provides a line showing of the movement of the subject with respect to a centerline along said predetermined path.

14. The motion analysis system of claim 1, wherein said data output means provides a cyclogram showing of the angles of movement of one joint of the subject with respect to the angles of movement of another joint of the subject for a predetermined cycle of movement.

15. The motion analysis system of claim 14, wherein the joints analyzed are hip and knee joints of the subject and said predetermined cycle of movement is a step undertaken with walking.

16. The motion analysis system of claim 15, wherein said data output means provides a visual display.

17. The motion analysis system of claim 15, wherein said data output means provides a hard copy printout display.

18. A motion analysis system as in claim 1 and in which said first program coacting with said minicomputer means further provides establishing the location, on a frame, of a pixel representing a marker means when said minicomputer fails to respond to a pixel of any gray level, the location being established by interpolation using atleast one sequentially prior frame and atleast one sequentially subsequent frame in which said minicomputer had responded to a pixels at the approximate horizontal and vertical coordinates of the missed pixel.

* * * * *

UNITED STATES PATENT AND TRADEMARK OFFICE
CERTIFICATE OF CORRECTION

PATENT NO. : 4,631,676
DATED : December 23, 1986
INVENTOR(S) : James W. Pugh

It is certified that error appears in the above-identified patent and that said Letters Patent is hereby corrected as shown below:

On the Title Page add

-- [73] Assignee: Hospital For Joint Diseases Orthopaedic Institute, New York, N. Y. --.

This certificate supersedes Certificate of Correction issued June 2, 1987.

Signed and Sealed this

Fifteenth Day of September, 1987

Attest:

DONALD J. QUIGG

*Attesting Officer*    *Commissioner of Patents and Trademarks*